United States Patent [19]

Gilbard

[11] 4,371,522

[45] Feb. 1, 1983

[54] KERATOCONJUNCTIVITIS SICCA THERAPY

[76] Inventor: Jeffrey P. Gilbard, 20 Mt. Vernon St., Boston, Mass. 02108

[21] Appl. No.: 209,832

[22] Filed: Nov. 24, 1980

Related U.S. Application Data

[63] Continuation-in-part of Ser. No. 27,294, Apr. 25, 1979, abandoned.

[51] Int. Cl.³ .............................................. A61K 33/14
[52] U.S. Cl. ................................................... 424/153
[58] Field of Search ......................................... 424/153

[56] References Cited

U.S. PATENT DOCUMENTS 2,547,653 4/1951 Minnis et al. ........................ 424/153
4,039,662 8/1977 Hecht et al. ......................... 424/180

OTHER PUBLICATIONS

Chem. Abst. 63, 16,126(e–f), (1965), Grosz et al.
Contact Lenses Practice, 2nd Ed., Mandell, p. 513, (1977).
Int. Ophthal. Clin. 13, 145–153, (1973), Lemp, "Tear Substitute in the Treatment of Dry Eye".
Int. Ophthal. Clin. 13, 221–229, (1973), Lemp, "Artificial Tear Solution".
Handbook of Non-Prescription Drugs, 5th Ed., pp. 228–232 & 234–235, (1977).

*Primary Examiner*—Douglas W. Robinson
*Attorney, Agent, or Firm*—Omri M. Behr

[57] ABSTRACT

Discomfort in patients suffering from keratoconjunctivitis sicca is considerably relieved by instilling into the eyes of the afflicted patient a small amount of hypotonic solution suitably of a strength of between 25 and 75 percent isotonicity.

7 Claims, 1 Drawing Figure

Patients 1-4 pooled.( 30 Kinetic studies in 8 eyes)

KERATOCONJUNCTIVITIS SICCA THERAPY

RELATED APPLICATIONS

This application is a continuation in part of application Ser. No. 027,294 filed Apr. 25, 1979 now abandoned.

BACKGROUND OF THE INVENTION

The disorder known as keratoconjunctivitis sicca (hereinafter KCS) was previously believed to generate its symptoms due to the formation of dry spots or incomplete wetting of the ocular surface. More recent work has shown that this theory is probably incorrect. The concept of the symptoms of the disease being due to an increased concentration of sodium chloride in the tear film was first postulated by Balik (Am. J. Ophthalmol 35, 773 (1952). Although Balik automatically rejected this postulate since he was unable to demonstrate the increase, support for this postulate was ultimately provided by Mishima et al (Ophthalmology, Proceedings of the XXI International Congress, Mexico, DF 8-14 March, 1970; Amsterdam, Excerpta Medica, 1971, pt 2, pp 1801 through 1805).

In the results obtained by Applicant and co-workers (Gilbard et al), Arch Ophthalmol 96 677, 1978, it was shown that in the 38 samples taken from 33 normal eyes a tear osmolarity of $304 \pm 10.4$ mOsm/l. was obtained while in the 38 samples from 30 KCS eyes osmolarity of $343 \pm 32.3$ mOsm/l. was obtained. By comparison it is noted that 8 eyes showing conjunctivitis (but not KCS) had a tear osmolarity of $298 \pm 6.1$ mOsm/l.

It has been postulated that the actual value of tear film osmolarity is a function of tear secretion and evaporation. Thus, if there is a decrease in the rate of tear secretion, tear film osmolarity will rise as the volume of freshly secreted isotonic tear fluid becomes inadequate to overcome the tendency of evaporation to increase tear film osmolarity.

In order to quantify the change in tear film osmolarity, Applicant developed a new appratus and method of using same for measuring tear film osmolarity which is reported in the foregoing reference (Arch Ophthalmol 96 677, 1978).

SUMMARY OF THE INVENTION

It has been found that administering ophthalmically acceptable hypotonic solution, suitably hypotonic buffered saline, to patients suffering from KCS, gives considerable relief from the symptoms of KCS.

BRIEF DESCRIPTIONS OF THE DRAWINGS

FIG. 1 shows the statistically pooled results obtained in an experiment utilizing substantially isotonic saline (circa 300 mOsm/l) and hypotonic saline (75-225 mOsm/l) where the osmolarity is measured over a 40 min. period.

DESCRIPTION OF THE PREFERRED EMBODIMENT

Figure 1:
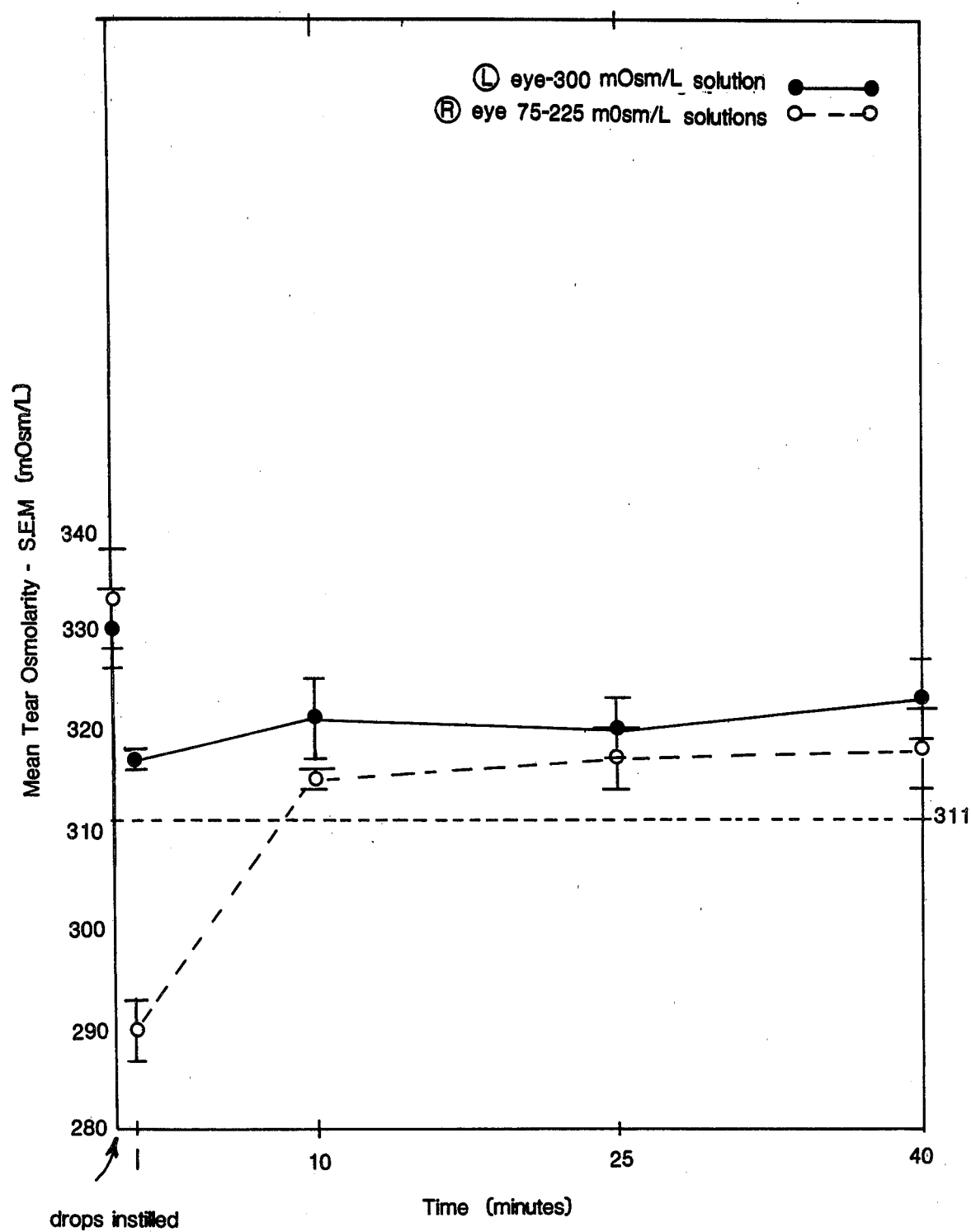

It is preferred to utilize hypotonic solutions of between about 25 to about 75 percent isotonicity (i.e. 75 to 225 mOsm/l, preferably 110 to 225 mOsm/l.) of which between 1 and 5 drops are instilled into the afflicted eyes at intervals of between about 0.5 to about 5 hours, or as needed, while the patient is awake.

The ophthalmically acceptable solutions suitable for this purpose include aqueous solutions of: sodium chloride, potassium chloride, dextrose, sucrose, methylcellulose, polyethylene glycol, and polyvinyl alcohol; these may be buffered by, for example, acetic acid, boric acid, phosphoric acid, potassium- or sodium-bicarbonates, biphosphates, borates, carbonates, citrates, or phosphates as well as triethanolanine. The foregoing components are designated as preferred components; however, the present invention should not be limited thereto. Any solutions which are physiologically acceptable in an ophthalmic context may be employed. It is preferred that the foregoing solutions be buffered to a pH of between 4.5 and 7.8. Nevertheless, this pH range need not be adhered to rigidly, provided the general criterion of physiological acceptability in an ophthalmic context is maintained.

The mode of administration of the hypotonic solution is not critical, however, or limited to the administration of eye drops (said eye drops having a volume of approximately 0.015 to 0.040 ml each). It is contemplated that the eye bath of the type disclosed by Holland, U.S. Pat. No. 3,906,949 may be used. It is contemplated that such an eye bath would be utilized in the initial stages of treatment in order to provide maximum relief as quickly as possible.

While Applicant does not wish to be limited thereby, it is believed that in KCS afflicted patients, as the tear film becomes hypertonic, the surface adjacent to it will also become hypertonic as a result of the osmotic exit of water from the ocular surface. This osmotic flow can presumably be reversed. Therefore, if the tonicity of the eye environment is substantially reduced by the administration of hypotonic solution the tonicity of the adjacent cells will similarly be reduced and thus, after removal of the external source of hypotonicity, that is to say the eye bath or the eye drops, the lower osmolarity of the ocular surface cells will compensate for the increasing tonicity of the tear film itself and provide relief for a continuing period of time. It should be noted, however, that it is not possible to reduce the tonicity of the eye environment drastically by the administration of water rather than a hypotonic solution. The administration of water brings about other undesirable symptoms similar to the "burning effect" demonstrated by the hypertonicity noted in KCS itself.

While a certain measure of relief from KCS symptoms may be obtained by an administration of isotonic saline, qualitative experments upon patients show that the measure of relief in patients is substantially greater where hypotonic solutions are utilized as contrasted with isotonic solutions.

It will be seen that a substantial amount of improvement in the osmolarity is noted over the first 20 minutes in contrast to that noted by administration of the isotonic solution. Since only 3 drops are instilled at the beginning of this time period, the reduced osmolarity readings would not be due only to the residual presence of the instilled drops, since it is known that aqueous solutions instilled into the eye are excreted within 60 seconds of instillation.

EXPERIMENTAL

In vivo human tests were carried out on patients afflicted with KCS. Five test solutions were used. Solution 1 (300 mOsm/l) is considered substantially isotonic. Solutions 2-5 are hypotonic.

The solutions utilized have the following osmolarity.

Solution 1: 300 mOsm/L sodium chloride solution. (Actual measured osmolarity was 303 mOsm/L.)
  Sodium chloride: 942 mg
  disodium EDTA: 10 mg
  benzalkonium chloride: 30 mg
  distilled water up to a total volume of 100 ml (solution was buffered with 0.2 N sodium hydroxide to a pH of 7)

Solution 2: 225 mOsm/L saline solution (measured osmolarity was 224 mOsm/L):
  Sodium chloride: 703 mg
  disodium EDTA: 10 mg
  benzalkonium chloride: 30 mg
  distilled water up to a total volume of 100 ml (solution was buffered with 0.2 N sodium hydroxide to a pH of 7)

Solution 3: 150 mOsm/L saline solution (measured osmolarity was 152 mOsm/L):
  Sodium chloride: 466 mg
  disodium EDTA: 10 mg
  benzalkonium chloride: 30 mg
  distilled water up to a total volume of 100 ml (solution was buffered with 0.2 N sodium hydroxide to a pH of 7)

Solution 4: 110 mOsm/L saline solution (measured osmolarity was 111 mOsm/L)
  Sodium chloride: 340 mg
  disodium EDTA: 10 mg
  benzalkonium chloride: 30 mg
  distilled water up to a total volume of 100 ml (solution was buffered with 0.2 N sodium hydroxide to a pH of 7)

Solution 5: 75 mOsm/L saline solution (measured osmolarity was 78 mOsm/L)
  Sodium chloride: 230 mg
  disodium EDTA: 10 mg
  benzalkonium chloride: 30 mg
  distilled water up to a total volume of 100 ml (solution was buffered with 0.2 N sodium hydroxide to a pH of 7)

Tear film osmolarity was studied serially in four keratoconjunctivitis sicca patients following instillation in the eye of four tear diluent solutions ranging in concentration from 75 mOsm/L to 225 mOsm/L, and also following instillation of isotonic saline. The tear diluent concentrations tested were 75 mOsm/L, 110 mOsm/L, 150 mOsm/L and 225 mOsm/L. In 15 trials (all left eyes) isotonic saline lowered tear film osmolarity to normal, that is below 312 mOsm/L, at one minute after instillation in only three eyes, or 20% of the eyes tested. In 15 trials on the same days (all right eyes), the tear diluent solutions lowered tear osmolarity to normal at one minute in 14 eyes, or 93.3% of the eyes tested, (patients 1–4, Table 1).

Average tear film osmolarity at one minute after instillation of tear diluents was significantly lower than after instillation of isotonic saline ($290 \pm 3$ mOsm/L vs. $317 \pm 1$ mOsm/L, $P < 0.0005$).

While both tear diluent and isotonic saline produced decreases in tear film osmolarity, the decrease following instillation of isotonic saline was significant for only 25 minutes, while the decrease following instillation of tear diluent was still significant at 40 minutes after drop instillation (FIG. 1, Table 2).

Two patients briefly experienced a mild burning sensation and one a mild itching sensation prior to obtaining improvement from the 75 mOsm/L tear diluent. There were no other complaints of discomfort with the use of these solutions. One patient experienced no initial discomfort from the 75 mOsm/L solution, but received immediate improvement in her symptoms. The data demonstrate that tear diluents are superior to isotonic solutions in lowering tear film osmolarity to normal, and that they produce a decrease in tear film osmolarity for a longer period of time after instillation in the eye.

TABLE 1

Tear osmolarity kinetics in four Keratoconjunctivitis sicca patients

|  | Osmolarity* of instilled drops | Tear Osmolarity Prior to eye drops | Tear Osmolarity after instillation of eye drops: | | | |
|---|---|---|---|---|---|---|
|  |  |  | 1 min | 10 min | 25 min | 40 min |
| Pat. one (B.V.) | 300 | 318 | 321 | 325 | 314 | 296 |
|  | 225 | 315 | 305 | 311 | 307 | 296 |
|  | 300 | 327 | 318 | 313 | 316 | 311 |
|  | 150 | 334 | 298 | 322 | 301 | 297 |
|  | 300 | 317 | 312 | 316 | 313 | 322 |
|  | 110 | 319 | 286 | 314 | 308 | 305 |
|  | 300 | 316 | 322 | 325 | 313 | 328 |
|  | 75 | 322 | 293 | 315 | 313 | 325 |
|  | **300 | 308 | 318 | 328 | 312 | 313 |
|  | **75 | 303 | 287 | 305 | 307 | 311 |
| Pat. two (E.H.) | 300 | 343 | 316 | 320 | 343 | 346 |
|  | 225 | 324 | 313 | 315 | 332 | 331 |
|  | 300 | 336 | 325 | 354 | 327 | 351 |
|  | 150 | 368 | 297 | 316 | 320 | 348 |
|  | 300 | 354 | 319 | 342 | 328 | 327 |
|  | 110 | 331 | 282 | 324 | 329 | 327 |
|  | 300 | 342 | 324 | 331 | 335 | 338 |
|  | 75 | 321 | 289 | 327 | 336 | 325 |
| Pat. three (J.O.) | 300 | 328 | 319 | 322 | 327 | 333 |
|  | 225 | 332 | 305 | 318 | 324 | 314 |
|  | 300 | 323 | 317 | 321 | 322 | 318 |
|  | 150 | 324 | 264 | 310 | 317 | 326 |
|  | 300 | 322 | 308 | 319 | 315 | 318 |
|  | 110 | 371 | 267 | 307 | 313 | 314 |
|  | 300 | 322 | 316 | 308 | 318 | 328 |
|  | 75 | 322 | 284 | 316 | 320 | 315 |
| Pat. four (D.K.) | 300 | 327 | 316 | 310 | 304 | 316 |
|  | 150 | 327 | 285 | 315 | 311 | 313 |
|  | 300 | 357 | 309 | 304 | 320 | 310 |
|  | 110 | 377 | 291 | 315 | 298 | 340 |
|  | 300 | 315 | 307 | 303 | 300 | 302 |
|  | 75 | 313 | 285 | 307 | 320 | 287 |
|  | **300 | 311 | 300 | 292 | 306 | 297 |
|  | **200 | 302 | 288 | 301 | 311 | 304 |

*All osmolarities are expressed as mOsm/L
**Omitted from statistical calculations because of initial normal osmolarity

TABLE 2

Pooled data from kinetic studies in four KSC+ patients.
(30 Kinetic studies, 150 tear osmolarity determinations in 8 eyes)

| Osmolarity* of instilled drops | Tear osmolarity prior to eye drops (mean + S.E.M) | Tear osmolarity after instillaton of eye drops (mean + S.E.M) | | | |
|---|---|---|---|---|---|
|  |  | 1 min | 10 min | 25 min | 40 min |
| 300 | 330 ± 4 | 317 ± 1 | 321 ± 4 | 320 ± 3 | 323 ± 4** |
| 75–225 | 335 ± 5 | 290 ± 3 | 315 ± 1 | 317 ± 3 | 318 ± 4 |

*All osmolarities are expressed as mOsm/L
**Does not represent a significant decrease compared to tear osmolarity prior to isotonic drops
+Keratoconjunctivitis sicca

I claim:

1. A method of relieving discomfort in eyes of patients afflicted with keratoconjunctivitis sicca which comprises adjusting the tonicity of the eyes by contacting the eyes of said patients with an ophthalmically acceptable hypotonic solution of a concentration of between 75 to 225 mOsm/l.

2. A method of claim 1 wherein the concentration is between about 110 and 225 mOsm/l.

3. A method of claim 1 wherein the hypotonic solution comprises substantially an aqueous solution of sodium chloride.

4. A method of claim 1 wherein the solution is buffered to a pH of between 4.5 and 7.8.

5. A method of claim 1 wherein the mode of contacting is bathing the afflicted eye with said hypotonic solution.

6. A method of claim 1 wherein the mode of contacting is instilling said hypotonic solution into the afflicted eye.

7. A method of claim 6 which comprises instilling between 1 and 5 drops (0.015 to 0.2 ml) into each affected eye at intervals of between 0.5 and 5 hours, or as needed, while the patient is awake.

* * * * *